United States Patent
Paz et al.

(10) Patent No.: US 7,473,822 B1
(45) Date of Patent: Jan. 6, 2009

(54) SOYBEAN TRANSFORMATION AND REGENERATION USING HALF-SEED EXPLANT

(75) Inventors: Margie Margarita M. Paz, Ames, IA (US); Kan Wang, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 406 days.

(21) Appl. No.: 11/475,318

(22) Filed: Jun. 27, 2006

Related U.S. Application Data

(60) Provisional application No. 60/694,410, filed on Jun. 27, 2005.

(51) Int. Cl.
*C12N 15/82* (2006.01)
(52) U.S. Cl. .................... 800/312; 800/294; 800/298
(58) Field of Classification Search ............... None
See application file for complete search history.

(56) References Cited

OTHER PUBLICATIONS

Ko et al., Theoretical and Applied Genetics, 2003; vol. 107, pp. 439-447.*
Paz et al., "Improved cotyledonary node method using an alternative explant derived from mature seed for efficient *Agrobacterium*-mediated soybean transformation," *Plant Cell Rep.*, 25:206-213 (2006).

* cited by examiner

*Primary Examiner*—Russell Kallis
(74) *Attorney, Agent, or Firm*—Carol Larcher; Larcher + Chao LLP

(57) ABSTRACT

A method of transforming soybean comprising infecting half-seed explants of soybean with *Agrobacterium tumefaciens* containing a transgene, which method can further comprise regenerating the half-seed explants in vitro on selection medium.

6 Claims, No Drawings

SOYBEAN TRANSFORMATION AND REGENERATION USING HALF-SEED EXPLANT

CROSS REFERENCE TO RELATED APPLICATION

This application claims priority to U.S. provisional patent application No. 60/694,410, which was filed on Jun. 27, 2005, and which is hereby incorporated by reference in its entirety.

TECHNICAL FIELD OF THE INVENTION

The present invention relates to *Agrobacterium*-mediated transformation and regeneration of soybean.

BACKGROUND OF THE INVENTION

Currently, soybean is transformed and regenerated using the cotyledonary node ("coty node") method or the embryogenic callus culture ("callus") method. The coty node method involves wounding the cotyledonary nodes on 5-7 day-old seedlings and co-cultivating the wounded seedlings with *Agrobacterium tumefaciens* for five days in the dark. Afterwards, plants are regenerated in tissue culture. The callus method involves particle bombardment of embryogenic tissue with DNA-coated carrier particles of inert material.

The coty node method is disadvantageous because it requires in vitro germination, precise wounding of the adaxial side of the cotyledonary node, which can result in poor reproducibility and non-germline transformation, which does not transmit the transgene to the progeny. Transformation efficiency typically ranges from 0.3 to 2.8%. The callus method is disadvantageous because it requires prolonged tissue culture, often yields complex insertion of genes into the plant genome, and may result in the regeneration of sterile plants.

The present invention seeks to provide an easier, more reproducible, more efficient, and more robust method of *Agrobacterium*-mediated transformation and regeneration of soybean. With the present invention, transformation efficiency typically ranges from 3.2 to 8.7%, with an overall efficiency of 4.9%. The method does not involve seed germination prior to explant preparation, nor does it involve deliberate and precise manual wounding. Other objects and advantages, as well as additional inventive features, will become apparent from the detailed description provided herein.

BRIEF SUMMARY OF THE INVENTION

The present invention provides a method of transforming soybean. The method comprises infecting half-seed explants of soybean with *Agrobacterium tumefaciens* containing a transgene. The method can further comprise regenerating the half-seed explants in vitro on selection medium.

DETAILED DESCRIPTION OF THE INVENTION

The present invention provides a method of transforming soybean. The method comprises infecting half-seed explants of soybean with *Agrobacterium tumefaciens* containing a transgene.

Mature soybean seeds are imbibed with water, preferably after surface-sterilization. Any suitable method of surface sterilization can be used. A preferred method of surface-sterilization is described in Example 1. The seeds are preferably imbibed in sterile, distilled water at room temperature for a sufficient amount of time to saturate the cotyledons, such as overnight or around 12-16 hours. A preferred method of imbibition is described in Example 1.

"Half-seed explants" refers to separated cotyledonous tissues that are derived from mature soybean seeds by splitting the cotyledons along the hilums and removing the seed coats, the primary shoots and the embryonic axes, which are found at the junctions of the hypocotyls and the cotyledons. Preferably, the seeds are surface-sterilized and then imbibed. Thus, a preferred embodiment of a half-seed explant is a cotyledonous tissue derived from a mature soybean seed, which has been surface-sterilized, imbibed, and separated into cotyledons along the hilum, and from which the seed coat, the primary shoot, and the embryonic axis have been removed. Desirably, the half-seed explants are not pre-treated with sucrose before infection with *A. tumefaciens* inasmuch as transformation efficiency is adversely affected.

The half-seed explants are infected with *A. tumefaciens* containing a transgene (any gene desired to be introduced into and expressed in soybean) in accordance with methods known in the art. Preferred methods are exemplified herein. Preferably, the explants are infected with *A. tumefaciens* in the presence of one or more agents that inhibit browning, such as anti-oxidants. Examples of agents that inhibit browning include, but are not limited to, cysteine, dithiothreitol (DTT), silver nitrate, and sodium thiosulfate. Preferably, cysteine is used in combination with one or more of DTT, silver nitrate, and sodium thiosulfate.

Co-cultivation is desirably conducted in the light inasmuch as co-cultivation in the dark results in half-seed explants, which fail to recover fully and which induce shoots marginally when incubated in the light during shoot induction. Co-cultivation of half-seed explants infected with *Agrobacterium* under around 140 µmoles $sec^{-1} m^{-2}$ light intensity for around 18 hours is preferred. Also, co-cultivation is desirably conducted in the absence of vacuum inasmuch as transformation efficiency is adversely affected to such an extent that no regeneration is obtained. Sonication is not required to assist infection with *Agrobacterium*.

The method can further comprise regenerating the half-seed explants in vitro on selection medium in accordance with methods known in the art. Preferred methods are exemplified herein. Preferably, the selection medium contains glufosinate, such as 6 mg/l glufosinate. Bialaphos can be used in place of glufosinate; however, transformation is more efficient when glufosinate is used and the incidence of escapes, i.e., non-transgenic shoots that survive glufosinate selection in vitro, is reduced.

The method generally enables the production of transgenic plants within 9-12 months of transformation. In this regard, any suitable genotype of soybean can be transformed and regenerated in accordance with the method. Examples of suitable genotypes include, but are not limited to, Thorne (Illinois Foundation Seed, Inc., Champaign, Ill.), Williams (USDA, ARS Soybean Germplasm Collection, Urbana, Ill.), Williams79 (Illinois Foundation Seed, Inc.), Williams82 (MG III) (Illinois Foundation Seed, Inc.), and Clinton (University of Guelph, Canada).

EXAMPLES

The following examples serve to illustrate the present invention. The examples are not intended to limit the scope of the invention in any way.

Example 1

This example describes the preparation of half-seed explants.

Mature Thorne soybean seeds were surface-sterilized for 16 hrs using chlorine gas, which was produced by mixing 3.5 ml of 12 N HCl with 100 ml of commercial bleach (5.25% sodium hypochloride) (Di et al., Plant Cell Rep. 15: 746-750 (1996)). Disinfected seeds were soaked in sterile, distilled water at room temperature (RT) for 16 hrs, 24 hrs, or 48 hrs (100 seeds in a 25×100 mm petri dish). The seeds were then split by cutting longitudinally along the hilums to separate the cotyledons, and the seed coats, primary shoots, and embryonic axes were removed, thereby generating half-seed explants. The half-seed explants were co-cultivated with *A. tumefaciens* for five days in the light.

Explants that were derived from seeds soaked in distilled water for 48 hrs gave a relatively higher rate of shoot induction (see Table I).

TABLE I

| Treatment | Reg. Freq. (%)[a] | Freq. GUS blue[b] | No. of Liberty-resistant $R_0$ plants | Initial Transformation Efficiency (ITE; %)[c] |
|---|---|---|---|---|
| Seeds soaked in water: | | | | |
| 16 hrs | 15/39 (38) | 12/12 (100%) | 5 | 12.9 |
| 24 hrs | 26/41 (58) | 9/9 (100%) | 7 | 17.1 |
| 48 hrs | 25/35 (66) | 9/10 (90%) | 3 | 8.6 |
| Seeds soaked in BAP: | | | | |
| control (water) | 28/50 (56) | 6/11 (54%) | 0 | 0.0 |
| 7.5 μM | 4/50 (8) | 1/10 (10%) | 0 | 0.0 |
| 15 μM | 24/50 (48) | 2/10 (20%) | 3 | 6.0 |
| 30 μM | 29/50 (58) | 9/10 (90%) | 2 | 4.0 |
| 50 μM | 23/50 (46) | 6/9 (67%) | 0 | 0.0 |

[a]regeneration frequency at first shoot induction stage
[b]observation of GUS blue on the section of explant where shoots were induced
[c]ITE = no. of Liberty-resistant $R_0$ events/no. of explants infected

Example 2

This example describes the strain of *Agrobacterium* and the transformation vector used to exemplify the method of transformation and regeneration.

The plant transformation construct pTF102 was derived from the base vector pTF101.1 (Paz et al., Euphytica 136: 167-179 (2004)) and was introduced into *A. tumefaciens* strain EHA101 (Hood et al., J. Bacteriol. 168: 1291-1301 (1986)). The construct pTF102 (Frame et al., Plant Physiol. 129: 13-22 (2002)) was derived from pTF01.1 by inserting the p35S GUS intron cassette (Vancanneyt et al., Mol. Gen. Genet. 220: 245-250 (1990)), which is driven by a CaMV 35S promoter, into the Hin dIII site of the multiple cloning site of pTF101.1. The GUS intron cassette prevents background GUS activity from contaminated *Agrobacterium* in plant tissue culture.

Example 3

This example describes the culture of *Agrobacterium* and the infection medium.

The construct pTF102 was maintained on YEP medium (An et al., Binary Vectors. In: Gelvin et al., eds. Plant Molecular Biology Manual A3, pp. 1-19. Kluwer Academic Publishers, Dordrecht. (1988)) containing 50 mg/l kanamycin, 100 mg/l spectinomycin, and 25 mg/l chloramphenicol. In every experiment, bacterial cultures used for infection of half-seed explants were initiated from plates grown at 28° C. for two days. Culture plates of the bacteria were stored for up to one month at 4° C. before being refreshed from long-term, −80° C. glycerol stocks. Fresh *Agrobacterium* single colonies were used to start a 2-ml liquid YEP culture containing appropriate antibiotics (8-10 hrs at 28° C., 250 rpm). Subsequently, a 250-ml YEP culture was initiated with 300-400 μl of the 2-ml starter culture, grown overnight to $OD_{650}$=0.7-1.0 at 28° C., 250 rpm using a shaker incubator. On the day of infection, a bacterial pellet was obtained by spinning the overnight culture at 3,500 rpm for 10 min. The pellet was resuspended in infection medium containing 1/10 strength Gamborg's B5 salts (Gamborg et al., Exp. Cell. Res. 50: 151-158 (1968)), B5 vitamins, and 1/5 strength MSIII iron stock (Murashige et al., Physiol. Plant 15: 473-479 (1962)), with 7.5 μM 6-benzylaminopurine (BAP), 0.7 μM gibberellic acid ($GA_3$), 20 mM 2-(N-morpholino)ethanesulfonic acid (MES), 3% sucrose, and 200 μM acetosyringone, pH 5.4. In all experiments, bacterial cell densities were adjusted to $OD_{650}$=0.7-0.8 using a spectrophotometer, prior to infection of half-seed explants.

Example 4

This example describes the infection of half-seed explants with *A. tumefaciens*.

About 50-100 half-seed explants were inoculated with 30 ml of *Agrobacterium* suspension culture in a 20×100 mm Petri dish at RT for 30 min. After inoculation, half-seed explants were transferred to co-cultivation medium lined with filter paper (6 explants per plate; flat side of explant in contact with filter paper) (see Table II). Co-cultivation was carried out for five days at 24° C. with 18 hr photoperiod at 140 μmoles $sec^{-1}m^{-2}$ light intensity.

TABLE II

| Chemicals | Stock | For 1 liter medium (ml) | Final Concentration |
|---|---|---|---|
| B5 major salts | 10x | 10 | 1/10x |
| B5 minor salts | 100x | 1 | 1/10x |
| MES | | 3.9 g | 20 mM |
| Sucrose | | 30 g | 3% |
| Acetosyringone | | 40 mg | 200 μM |
| B5 vitamin | 100x | 10 | 1x |
| BAP | 1 mg/ml | 1.67 | 7.5 μM |
| $GA_3$ | 1 mg/ml | 0.25 | 0.7 μM |
| Cysteine | | 400 mg | |
| Dithiothreitol | | 154 mg | |
| Noble agar | | 4.25 g | |
| pH 5.4 | | | |

Example 5

This example describes regeneration and selection.

After co-cultivation, the half-seed explants were washed in liquid shoot induction (SI) medium (see Table III). The explants were cultured on shoot induction medium solidified with 0.7% agar in the absence of selection. The base of the explant (i.e., the part of the explant from where the embryonic axis was removed) was embedded in the medium, facing upwards. When the cytokinin BAP was added to the shoot induction medium, the regeneration frequency differed significantly between treatments with treatment in the range of 15-100 μM providing enhanced shoot formation as compared to no treatment or treatment in the range of 2.5-7.5 μM. Shoot induction was carried out in a Percival Biological Incubator at 24° C. with an 18-hr photoperiod at 140 μmoles $sec^{-1}m^{-2}$ light intensity. After 14 days, the explants were transferred to fresh shoot induction medium containing 6 mg/l glufosinate. After four weeks of culture on shoot induction medium, explants were transferred to shoot elongation (SE) medium containing 6 mg/l glufosinate (see Table IV). Two to four weeks later, elongated shoots (>2.5 cm) were dipped in sterile IBA (1 mg/l) and then transferred to rooting medium (see Table V) without glufosinate. After two weeks, agar medium was rinsed off of the rooted plantlets with water, and the rooted plantlets were transplanted to soil (Redi-Earth, Peat-Lite Mix, Scotts-Sierra Horticultural Products Company, Marysville, Ohio) in jiffy pots. The plant (R0) was grown at 24° C. with an 18-hr photoperiod for one-two weeks and then transferred to the greenhouse.

TABLE III

Shoot Induction Medium

| Chemicals | Stock | For 1 liter medium (ml) | Final Concentration |
|---|---|---|---|
| B5 major salts | 10x | 100 | 1x |
| B5 minor salts | 100x | 10 | 1x |
| Ferrous-NaEDTA | 200x | 5 | 1x |
| MES | | 0.59 g | 3 mM |
| Sucrose | | 30 g | 3% |
| B5 vitamins | 100x | 10 | 1x |
| BAP | 1 mg/ml | 1.67 | 7.5 μM |
| Timentin | 100 mg/ml | 0.5 | 50 mg/l |
| Cefotaxine | 100 mg/ml | 2 | 200 mg/l |
| Vancomycin | 50 mg/ml | 1 | 50 mg/l |
| Glufosinate * | 20 mg/ml | 0-0.3 | 6 mg/l |
| Noble agar ** | | 7 g | |
| pH 5.7 | | | |

* added to SI liquid medium for selection during shoot induction stage
** added to SI liquid medium to generate solid medium

TABLE IV

Shoot Elongation Medium

| Chemicals | Stock | For 1 liter medium (ml) | Final Concentration |
|---|---|---|---|
| MS major salts | 10x | 100 | 1x |
| MS minor salts | 100x | 10 | 1x |
| Ferrous-NaEDTA | 200x | 5 | 1x |
| MES | | 0.59 g | 3 mM |
| Sucrose | | 30 g | 3% |
| B5 vitamins | 100x | 10 | 1x |
| Asparagine | 5 mg/ml | 10 | 50 mg/l |
| Pyroglutamic acid | 10 mg/ml | 10 | 100 mg/l |
| IAA | 1 mg/ml | 0.1 | 0.1 mg/l |
| $GA_3$ | 1 mg/ml | 0.5 | 0.5 mg/l |
| Zeatin-riboside | 1 mg/ml | 1 | 1 mg/l |
| Timentin | 100 mg/ml | 0.5 | 50 mg/l |
| Cefotaxine | 100 mg/ml | 2 | 200 mg/l |
| Vancomycin | 50 mg/ml | 1 | 50 mg/l |
| Glufosinate* | 20 mg/ml | 0.3 | 6 mg/l |
| Noble agar | | 7.0 | |
| pH 5.7 | | | |

*added to SE medium for selection during shoot elongation

TABLE V

Rooting Medium

| Chemicals | Stock | For 1 liter medium (ml) | Final Concentration |
|---|---|---|---|
| MS major salts | 10x | 100 | 1x |
| MS minor salts | 100x | 10 | 1x |
| Ferrous-NaEDTA | 200x | 5 | 1x |
| MES | | 0.59 g | 3 mM |
| Sucrose | | 20 g | 2% |
| B5 vitamins | 100x | 10 | 1x |
| Noble agar | | 7 g | |
| pH 5.6 | | | |

Shoot regeneration on half-seed explants of Thorne ranged from 42% to 76% across experiments (see Table VI). An adequate number of shoots was obtained on SE medium and transferred to soil for screening.

TABLE VI

Thorne Shoot Regeneration Rate

| Regeneration rate (%) | No. of shoots to soil |
|---|---|
| 21/39 (53.8) | 27 |
| 26/34 (76.0) | 15 |
| 28/50 (56.0) | 17 |
| 33/78 (42.0) | Ongoing |

Example 6

This example describes the response of different cultivars to transformation and regeneration using the half-seed explant method.

Half-seed explants of Thorne, Williams, Williams79, Williams82, Champion, and Clinton were infected with pTF102 and co-cultivated for five days in the light. Visual observations of transient GUS (blue) expression on half-seed explants indicated that T-DNA transfer was achieved following co-cultivation (Table VII). Stable GUS expression was obtained 28 days after co-cultivation, and GUS-positive shoots were observed in Thorne, Williams, Williams79, and Clinton. Williams82 and Champion showed GUS-positive sectors on the explant that did not regenerate shoots. Regeneration frequency did not differ significantly between Thorne, Williams, Williams79, and Williams82; regeneration frequency, however, was lower in Champion and Clinton. Shoot induction rates were lower (26-58%) in the cultivars tested here, as compared to rates reported using pTF102 to transform cotyledonary node explants (76-100%; Paz et al., Euphytica 136: 167-179 (2004)). *Agrobacterium*-mediated transformation of Lambert, MN1801, and IA1006 also was carried out, and shoot regeneration was attained in these genotypes.

TABLE VII

Cultivate Response to Transformation and Regeneration

| Cultivar | No. of explants Infected | Regeneration frequency (%)[a] | Frequency of transient GUS (%)[b] | No. of Gus blue shoots[c] |
|---|---|---|---|---|
| Thorne | 256 | 58 | 34/71 (49) | 6/46 |
| Williams | 147 | 52 | 18/30 (60) | 7/32 |
| Williams79 | 152 | 52 | 13/30 (43) | 1/11 |
| Williams82 | 214 | 50 | 12/30 (40) | 0/19 |

TABLE VII-continued

Cultivate Response to Transformation and Regeneration

| Cultivar | No. of explants Infected | Regeneration frequency (%)[a] | Frequency of transient GUS (%)[b] | No. of Gus blue shoots[c] |
|---|---|---|---|---|
| Champion | 60 | 27 | N/A[d] | 0/7 |
| Clinton | 62 | 26 | N/A | 2/11 |

[a]regeneration frequency = (no. explants with one or more shoots/no. of explants infected) × 100
[b](no. explants showing GUS blue/no. explants examined) × 100; data obtained after 5 days co-cultivation
[c](no. GUS blue shoots/no. explants examined) × 100
[d]N/A = not available Example 7

This example demonstrates in vitro shoot regeneration on half-seed explants.

Half-seed explants from imbibed Thorne seeds were sampled and fixed before infection with *A. tumefaciens* and at various times post-infection for viewing by scanning electron microscopy (SEM). The explants were fixed with 2% paraformaldehyde and 2% glutaraldehyde in 0.1 M cacodylate buffer, pH 7.3, for 24 hrs at 4° C. The samples were then washed in 0.1 M cacodylate buffer three times, and post-fixed with 1% osmium tetroxide in 0.1 M cacodylate buffer, pH 7.3, at RT for one hour. The samples were then rinsed three times with deionized distilled water (5 min/rinse) and dehydrated in a graded ethanol series into ultra pure ethanol. Tissue samples were dried using a Denton DCP-1 critical point dryer (Denton Vacuum, Inc., Moorestown, N.J.), mounted onto aluminum stubs, and sputter-coated with palladium-gold alloy (60/40) using a Denton Vacuum DeskII sputter coater (Denton Vacuum, Inc., Moorestown, N.J.). SEM of explants before and after infection was carried out at the Bessey Microscopy Facility at Iowa State University, Ames, Iowa. Images were captured digitally with the SIS ADDA II System (Soft Imaging System, Lakewood, Colo.) using a JEOL 5800LV scanning electron microscope (Japan Electron Optics Laboratory, Peabody, Mass.).

There was a preponderance of *A. tumefaciens* attached to the area of excision of the embryonic axis on the half-seed explant one day after infection. *A. tumefaciens* was persistently attached to plant cells after five days of co-cultivation. Tissue growth was detected on the half-seed explant at five days post-infection. After seven days, shoot formation was more evident. Further growth of induced shoot was observed after nine and 11 days.

Thirty-six putative $R_0$ transformants of Thorne, which were glufosinate-resistant after Liberty painting, were obtained. Initial transformation efficiency ranged from 3.2-8.7%, based on the number of glufosinate-resistant $R_0$ plants/number of infected explants (see Table VIII).

TABLE VIII

Thorne Transformation Efficiency

| No. of explants infected | No. of Southern-positive events in $R_1$ generation | Final transformation efficiency (FTE; %)[a] |
|---|---|---|
| 65 | 3 | 4.6 |
| 115 | 10 | 8.7 |
| 228 | 11 | 4.8 |
| 250 | 8 | 3.2 |
| 310 | 4 | 1.3[b] |

[a]FTE = (no. of Southern-positive $R_1$ events/no. of explants infected) × 100
[b]ongoing experiment Example 8

This example describes the screening of first generation transgenic plants ($R_0$ plants) and the testing of their progeny.

Herbicide Assay $R_0$ plants with two trifoliates were screened using the herbicide paint assay to identify putative transformants that expressed the bar gene. The upper surface of a leaf was painted with 150 mg/l glufosinate (herbicide Liberty®, AgrEvo, U.S.A.) along the midrib using a cotton bud. Plants were scored based on the tolerance of the leaf tissue to glufosinate at three-five days after painting. Glufosinate-resistant $R_0$ plants were grown in the greenhouse until maturity and seeds were harvested. Subsequently, seeds from $R_0$ plants were sown and progeny-tested to confirm the presence of the transgene in the $R_1$ generation by spraying two-week-old seedlings with 200 mg/l glufosinate. Plants were scored one week after spraying. Thirty-two transgenic events were confirmed in the $R_1$ progeny by spraying with 200 mg/l glufosinate using herbicide Liberty. Chi-square analysis for goodness of fit into a 3:1 pattern for a single locus showed the expected Mendelian (3:1) pattern in 26 of 30 events tested. Plants were fertile and produced seed.

GUS Assay

After five days of co-cultivation, half-seed explants infected with pTF102 were assayed for transient GUS blue expression to verify T-DNA transfer. The explants were incubated overnight in 5-bromo-4-chloro-3-indolyl glucuronide (X-gluc) solution at 37° C. (Jefferson et al., EMBO J 6: 3901-3907 (1987)). After staining, the explants were de-stained with 70% ethanol to improve contrast. The incidence of GUS activity was determined based on the presence of blue-staining areas. In addition, stable GUS expression was determined after 28 days on regeneration medium or on $R_0$ plants. The transgenic nature of the soybean plants was also confirmed in the $R_0$ or $R_1$ generation by histochemical GUS assay.

Molecular Analyses

Polymerase chain reaction (PCR) was done using primers for the bar gene. PCR reactions were carried out in a 25 μl reaction mixture containing 60 ng of genomic DNA, 100 μM each of dGTP, dATP, dCTP, and dTTP, 2.5 mM $MgCl_2$, 1× Bioline PCR buffer (Bioline USA, Inc., Randolph, Mass.), 0.15 μM of each primer, and 1.5 units of Biolase DNA polymerase (Bioline USA, Inc.). Thermal cycling conditions consisted of one cycle of 5 min at 95° C., 30 cycles of 45 sec at 95° C. (denaturation), 30 sec at 58° C. (annealing), and 30 sec at 72° C. (extension), and a final extension at 72° C. for 5 min. The amplified DNA products were analyzed on 1.0% agarose gel in 1×TBE buffer. The transgenic nature of the soybean plants was confirmed in the R0 or R1 generation by PCR analysis.

Southern blot analysis was done using 10 μg of genomic DNA digested with Xho I or Hin dIII. The restriction products were separated on a 0.8% agarose gel and hybridized with a $^{32}$P-labeled gus fragment. Glufosinate-resistant plants were Southern-positive.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention, unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of transforming soybean, which method comprises imbibing mature soybean seeds, excising the embryonic axis and the shoots of the imbibed mature soybean seeds prior to generation of seedlings, infecting the resulting half-seed explants of soybean with *Agrobacterium tumefaciens* containing a transgene, and selecting for transformants, whereupon the soybean is transformed and wherein the only wounding to the explants is excision of the embryonic axis and the shoots.

2. The method of claim 1, which further comprises regenerating the half-seed explants in vitro on selection medium, whereupon soybean is regenerated.

3. The method of claim 1, wherein the half-seed explants are infected with *A. tumefaciens* containing the transgene by co-cultivation in the presence of light.

4. The method of claim 2, wherein the selection medium contains glufosinate.

5. The method of claim 1, wherein the half-seed explants are infected with the *A. tumefaciens* containing the transgene in the presence of at least one agent that inhibits browning.

6. The method of claim 5, wherein the at least one agent that inhibits browning is cysteine, alone or in further combination with one or more of dithiothreitol, silver nitrate, and sodium thiosulfate.

* * * * *

UNITED STATES PATENT AND TRADEMARK OFFICE
CERTIFICATE OF CORRECTION

PATENT NO. : 7,473,822 B1 Page 1 of 1
APPLICATION NO. : 11/475318
DATED : January 6, 2009
INVENTOR(S) : Paz et al.

It is certified that error appears in the above-identified patent and that said Letters Patent is hereby corrected as shown below:

In Column 10, Claim 2, line 15, "in vitro" should be italicized to read:

--*in vitro*--

Signed and Sealed this

Seventh Day of April, 2009

JOHN DOLL
*Acting Director of the United States Patent and Trademark Office*